US007351746B2

(12) United States Patent
Zelkha et al.

(10) Patent No.: US 7,351,746 B2
(45) Date of Patent: Apr. 1, 2008

(54) ANTI-ATHEROSCLEROSIS COMPOSITION CONTAINING CAROTENOIDS AND METHOD FOR INHIBITING LDL OXIDATION

(75) Inventors: Morris Zelkha, Beer Sheva (IL); Tanya Sedlov, Beer Sheva (IL); Zohar Nir, Beer Sheva (IL)

(73) Assignee: Lycored Natural Products Industries Ltd., Beer Sheva (IL)

( * ) Notice: Subject to any disclaimer, the term of this patent is extended or adjusted under 35 U.S.C. 154(b) by 416 days.

(21) Appl. No.: 10/466,957

(22) PCT Filed: Jan. 21, 2002

(86) PCT No.: PCT/IL02/00053

§ 371 (c)(1),
(2), (4) Date: Jan. 14, 2004

(87) PCT Pub. No.: WO02/058682

PCT Pub. Date: Aug. 1, 2002

(65) Prior Publication Data

US 2004/0110849 A1 Jun. 10, 2004

(30) Foreign Application Priority Data

Jan. 23, 2001 (IL) .................................... 141039

(51) Int. Cl.
*A61K 31/01* (2006.01)

(52) U.S. Cl. ...................................... 514/762; 514/725

(58) Field of Classification Search .................... None
See application file for complete search history.

(56) References Cited

U.S. PATENT DOCUMENTS

| | | | | |
|---|---|---|---|---|
| 5,643,623 | A | 7/1997 | Schmitz et al. | |
| 6,132,790 | A * | 10/2000 | Schlipalius | 426/540 |
| 6,383,474 | B1 | 5/2002 | Soudant et al. | |
| 6,555,134 | B1 * | 4/2003 | Aviram et al. | 424/456 |
| 2002/0172729 | A1 * | 11/2002 | Kenton et al. | 424/757 |
| 2004/0191297 | A1 * | 9/2004 | Schlipalius et al. | 424/439 |

FOREIGN PATENT DOCUMENTS

| | | |
|---|---|---|
| EP | 1 175 898 | 1/2002 |
| EP | 1175898 | 1/2002 |
| WO | WO 98/57622 | 12/1998 |
| WO | WO 9857622 | 12/1998 |
| WO | WO 00/13654 | * 3/2000 |
| WO | WO 0013654 | 3/2000 |
| WO | WO 02/058683 | 8/2002 |
| WO | WO 02058683 | 8/2002 |

OTHER PUBLICATIONS

Medline Abstract No. 1999061302 of Paetau et al., The American Journal of Clinical Nutrition, (Dec. 1998), vol. 68, No. 6, pp. 1187-1195.*
HCAPlus Abstract No. 1998:592782 of Khachik et al., ACS Symposium Series (1998), 701 (Functional Foods for Disease Prevention I: Fruits, Vegetables, and Teas), 71-85.*
Webster's II New Riverside University Dictionary, published 1984 by The Riverside Publishing Company, p. 76, "active".*
Agarwal et al, "Tomato Lycopene and low density lipoprotein oxidation: a human dietary intervention study," *Lipids* 33: 981-984 (1998).
Bohm et al "Carotenoids protect against cell membrane damage by the nitrogen dioxide radical," *Nature Medicine* 2: 98-99 (1995).
Burton "Antioxidant action of carotenoids," *J. Nutr.* 119: 109-111 (1989).

(Continued)

*Primary Examiner*—Raymond J Henley, III
(74) *Attorney, Agent, or Firm*—Browdy and Neimark P.L.L.C.

(57) ABSTRACT

An anti-atherosclerosis composition comprising a LDL-oxidation inhibiting effective amount of phytoene, phytofluene or mixtures thereof and a method for inhibiting the progression of atherosclerosis.

6 Claims, 8 Drawing Sheets

OTHER PUBLICATIONS

Castelli et al "Lipids and risk of coronary heart disease, The Framingham Study," *Ann Epidemiol* 2 (1-2): 23-28 (1992).
Davies et al "Atherosclerosis: what is it and why does it occur," *Br Hear J.* 69: S3 (1993).
Dimascio et al "Lycopene as the most efficient biological carotenoid singlet oxygen quencher," *Arch. Biochem. Biophys.* 274: 532-538 (1989).
Fuhrman et al "Lycopene synergistically inhibits ldl oxidation in combination with vitamin E, glabridin, rosmarinic acid, carnosic acid, or garlic, Antioxidants and redox signaling," *Antioxoidants and Redox Signaling* 3: 491-506, date unavailable.
Fuhrman et al "Hypocholesterolemic effect of lycopene and b-carotene is related to suppression of cholesterol synthesis and augmentation of Ldl receptor activity in macrophages," *Biochemical and Biophysical research Communications* 233: 658-662 (1997).
Haberland "The role of altered lipoproteins in the pathogenesis of atherosclerosis," *A. Heart J.* 113: 573-577 (1987).
Fuhrman et al "Tomato lycopene and beta carotene inhibit low sensity lipoprotein oxidation and this effect depends on the lipoprotein vitamin E content," *NMCD Nutrition Metabolism and Cardiovascular Diseases* 7: 433-443 (1997).
Hennekens et al "Lack of effect of long-term supplementation with beta carotene on the incidence of malignant neoplasms and cardiovascular disease," *N. Engl. J. Med.* 334: 1145-1149, date unavailable.
Krinsky "Antioxidant functions of carotenoids," *Free Radic. Biol. Med.* 7: 617-635 (9-13) (1989).
Kohlmeier "Epidemiologic evidence of a role of carotenoids in cardiovascular disease prevention," *Am. J. Clin. Nutr.* 62: 137S-146S, date unavailable.
Steinberg et al "Beyond cholesterol: modification sof low-density lipoprotein that increase its atherogenicity" *N. Engl. J. Med.* 320: 915-924 (1989).
Witztum "The oxidation hypothesis of atherosclerosis," *Lancet* 344: 793 (1994).

* cited by examiner

A. TBARS
60
40
20
0
*
*

B. LIPID PEROXIDES
2500
2000
1500
1000
500
0
*
*
CuSO4-INDUCED LDL OXIDATION
(nmol/mg LDL protein)
Control
+Vitamin E (Vit E)
+Vit E + Lyc
+Vit E + β-Car
+Vit E + P/P

ANTI-ATHEROSCLEROSIS COMPOSITION CONTAINING CAROTENOIDS AND METHOD FOR INHIBITING LDL OXIDATION

FIELD OF THE INVENTION

The present invention relates to the field of natural products and uses thereof for inhibiting the progression of atherosclerosis. More particularly, the present invention relates to compositions comprising phytoene, phytofluene or mixtures thereof and their use for inhibiting the progression of atherosclerosis.

BACKGROUND OF THE INVENTION

The prevention of LDL oxidation has been acknowledged as an important factor in the inhibition of the progression of atherosclerosis. There is a variety of anti-atheosclerosis drugs such as the drugs of the vastatin group, hereinafter conventional anti-atherosclerosis agents. Furthermore, certain carotenoids which are known to be anti-oxidants have been reported to inhibit LDL oxidation and thus arrest the progression of atherosclerosis (see, e.g. Krinsky, N., *Free Radical Biology & Medicine*, (1989) vol. 7, pp. 617-635). PCT/IL98/00286 discloses the effectiveness of a synergistic mixture of lycopene and vitamin E in inhibiting LDL-oxidation, and hence arresting the progression of atherosclerosis. The effectiveness of the carotenoids phytoene and phytofluene in inhibiting LDL-oxidation has not been evaluated.

The contribution of atherosclerosis to heart disease is well known. Therefore there is a constant need for novel compositions which effectively inhibit the progression of atherosclerosis.

Accordingly, it is an objective of the present invention to provide a novel composition which demonstrates high effectiveness in inhibiting LDL oxidation, thus effectively arresting the progression of atherosclerosis.

A further objective of the present invention is to provide a method for inhibiting LDL oxidation and hence inhibit the progression of atherosclerosis.

Other objects of the invention will become apparent as the description proceeds.

SUMMARY OF THE INVENTION

The present invention provides a method for inhibiting the progression of atherosclerosis, comprising the administration of an effective anti-LDL-oxidation amount of phytoene, phytofluene or mixtures thereof, to a subject in need thereof.

Further provided by the present invention is the use of a composition comprising phytoene, phytofluene or mixtures thereof, for inhibiting the oxidation of LDL.

A further aspect of the present invention is the use of phytoene, phytofluene or mixtures thereof, in the preparation of a medicament for inhibiting the oxidation of LDL and the progression of atherosclerosis.

The present invention further provides an anti-atherosclerosis composition comprising a LDL-oxidation inhibiting effective amount of phytoene, phytofluene or mixtures thereof.

Further provided by the present invention is the use of a LDL-oxidation inhibiting effective amount of phytoene, phytofluene or mixtures thereof, in functional foods, dietary supplements, food stuff and drinks.

DETAILED DESCRIPTION OF A PREFERRED EMBODIMENT OF THE INVENTION

Figure 1A:
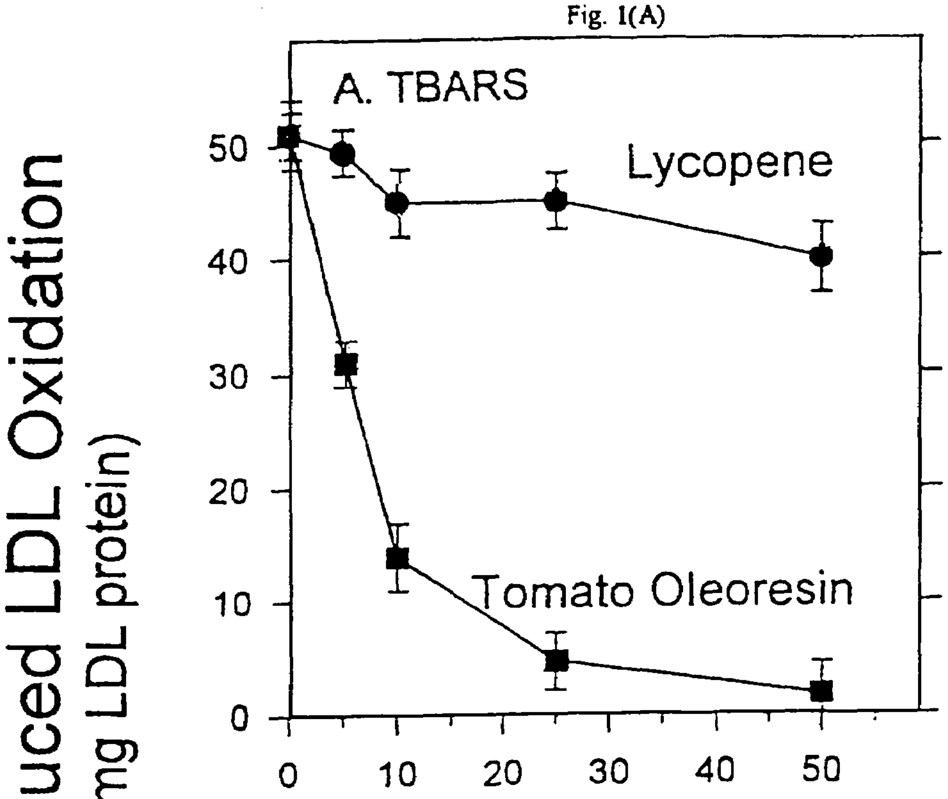
FIG. 1(A), (B)—Effect of crystalline natural lycopene and of tomato oleoresin on copper ion-induced LDL oxidation.

The following description is illustrative of preferred embodiments of the invention. The following description is not to be construed as limiting, it being understood that the skilled person may carry out many obvious variations to the invention.

The description applies to mixtures of phytoene and phytofluene as well as to each one of them separately. Therefore, wherever reference is made to mixtures thereof it is also intended for each of the carotenoids separately as well.

While studying the effect of various carotenoids on LDL oxidation it has been surprisingly found that phytoene, phytofluene or mixtures thereof, are substantially more effective than other carotenoids in inhibiting LDL oxidation.

According to a particular embodiment of the method of the present invention, at least 0.2 mg/day of phytoene, phytofluene or mixtures thereof, are administered to a subject in order to inhibit the oxidation of LDL in the blood and hence arrest the progression of atherosclerosis. Wherein a mixture of said carotenoids is administered, the ratio between phytoene and phytofluene in the mixture is from about 1:20 to 20:1. Administration may be in daily multiple or single dosages. According to the present method, administration is adopted to achieve an anti-LDL-oxidation effective concentration of phytoene, phytofluene or mixtures thereof, in the blood, said concentration being at least 0.01 μM.

According to an optional embodiment of the present method, phytoene, phytofluene or mixtures thereof, may be administered in conjunction with conventional anti-atherosclerosis agents.

According to a further aspect of the present invention there is provided a composition comprising an anti-LDL-oxidation effective amount of phytoene, phytofluene or mixtures thereof. Said composition comprising at least 0.1 mg of phytoene, phytofluene or mixtures thereof. The composition may further comprise pharmaceutically acceptable adjuvant, excipients and additives.

A further embodiment of the present invention relates to a solid dosage form for oral administration, in the form of a tablet, capsule, hard-shell capsule, soft gel or gelcap, which contains at least 0.1 mg of phytoene, phytofluene or mixtures thereof.

According to yet a further embodiment of the present invention, the use of phytoene, phytofluene or mixtures thereof, is provided wherein they are added to functional foods such as bars, dietary supplements, drinks or other food stuff so that said functional foods, dietary supplements, food stuff and drink provide an inhibitory effect on LDL-oxidation. According to the present embodiment the functional food, food stuff, dietary supplement or drink comprise at least 0.1 mg of of phytoene, phytofluene or mixtures thereof.

The following examples illustrate the substantially improved effectiveness of phytoene and phytofluene over other carotenoids, in the inhibition of LDL oxidation.

EXAMPLES

General Procedures

All studied compounds were dissolved in THF to a stock solution of 1 mg/ml. LDL was dialyzed for 24 hours against phosphate buffered-saline (PBS) prior to its oxidation to remove any EDTA that can interfere with the oxidation. LDL (100 μg protein/ml), was incubated in the absence (Control) or presence of increasing concentrations of each one of the studied compounds, as well as, in various combinations including 2, 3 or the 4 constituents at the desired natural distribution. LDL oxidation was induced by the addition of 5 μM of $CuSO_4$, for 2 hours at 37° C. LDL oxidation was terminated by adding 1 mM $Na_2$ EDTA and immediate refrigeration at 4° C. The extent of LDL oxidation was then determined by measuring the amount of thiobarbituric acid reactive substances (TBARS) and of lipid peroxides (PD) formed. Control LDL was supplemented with only THF.

Example 1

Figure 1B:
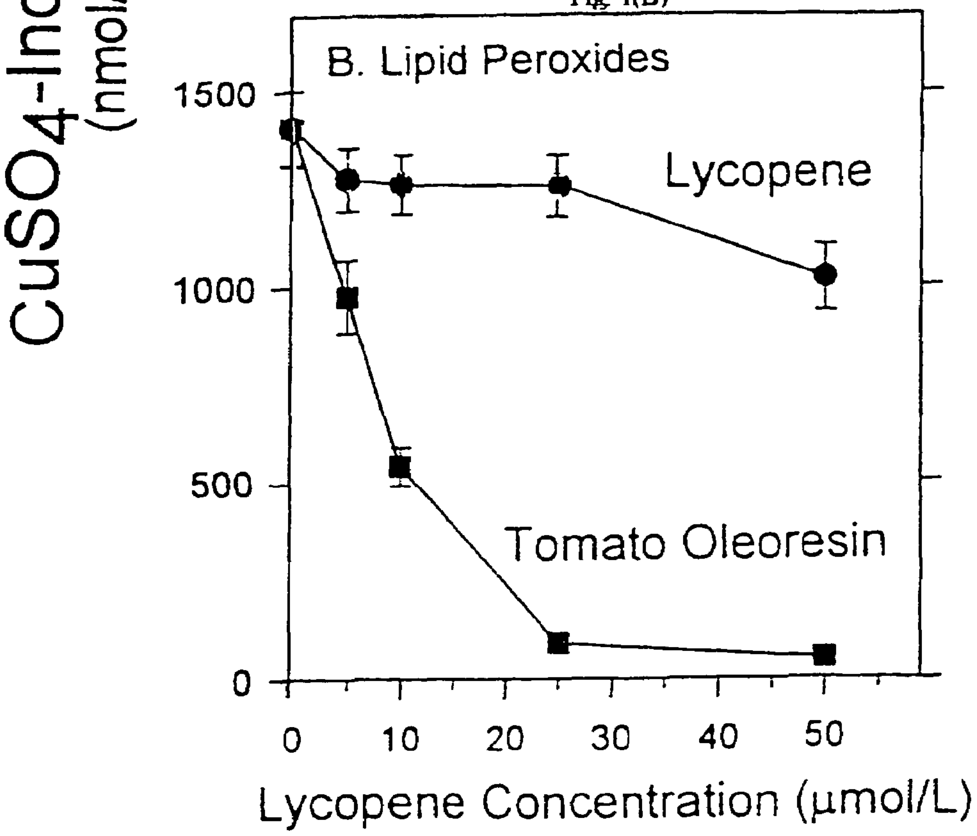
Figure 2A:
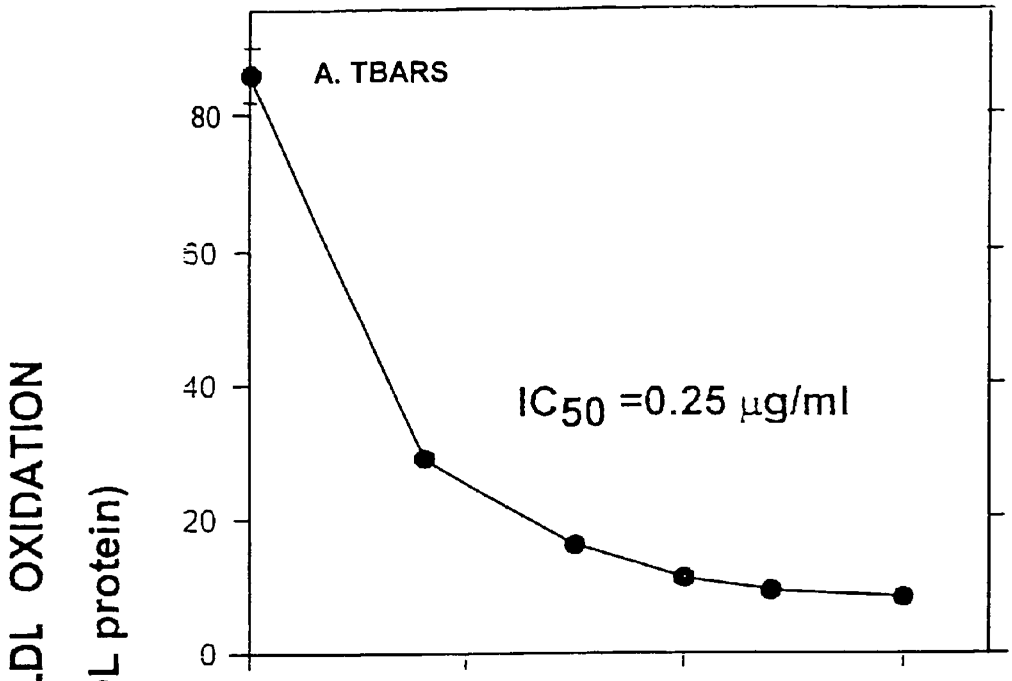
FIG. 2(A), (B)—Effect of Phytofluene/phytoene on copper ion-induced LDL oxidation.
Figure 2B:
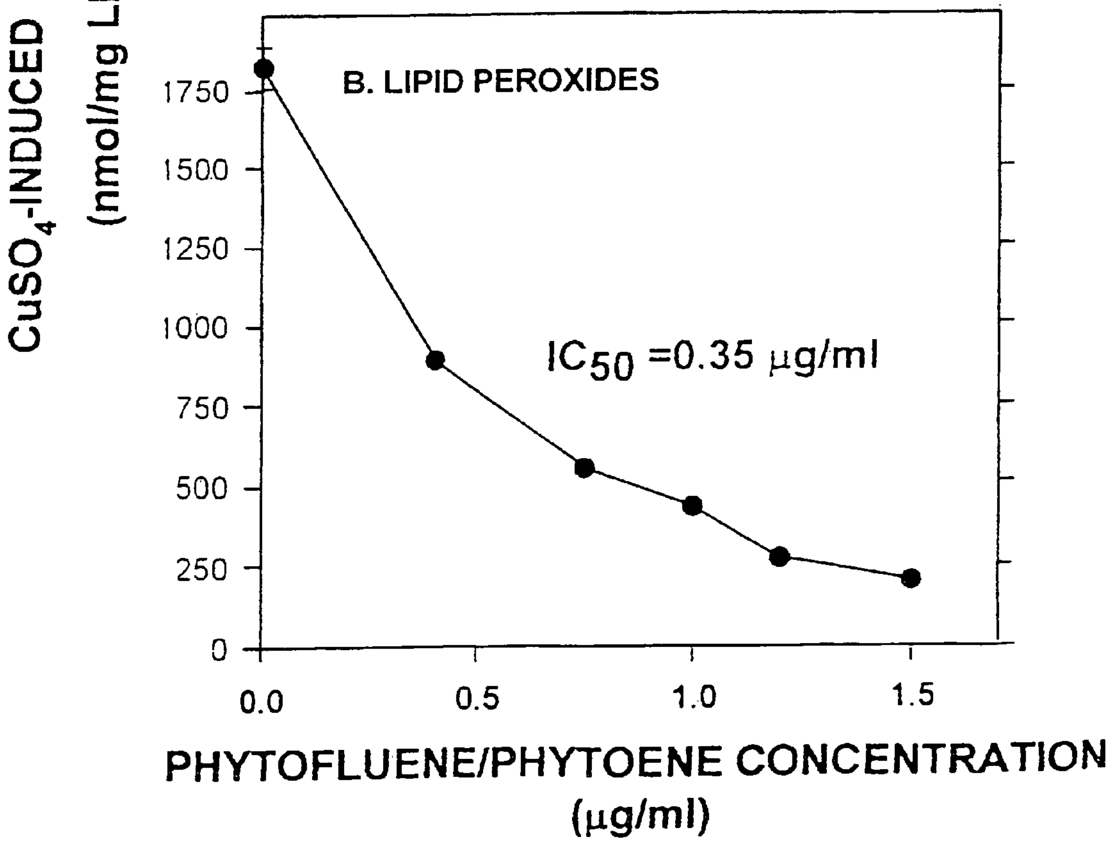
Figure 3A:
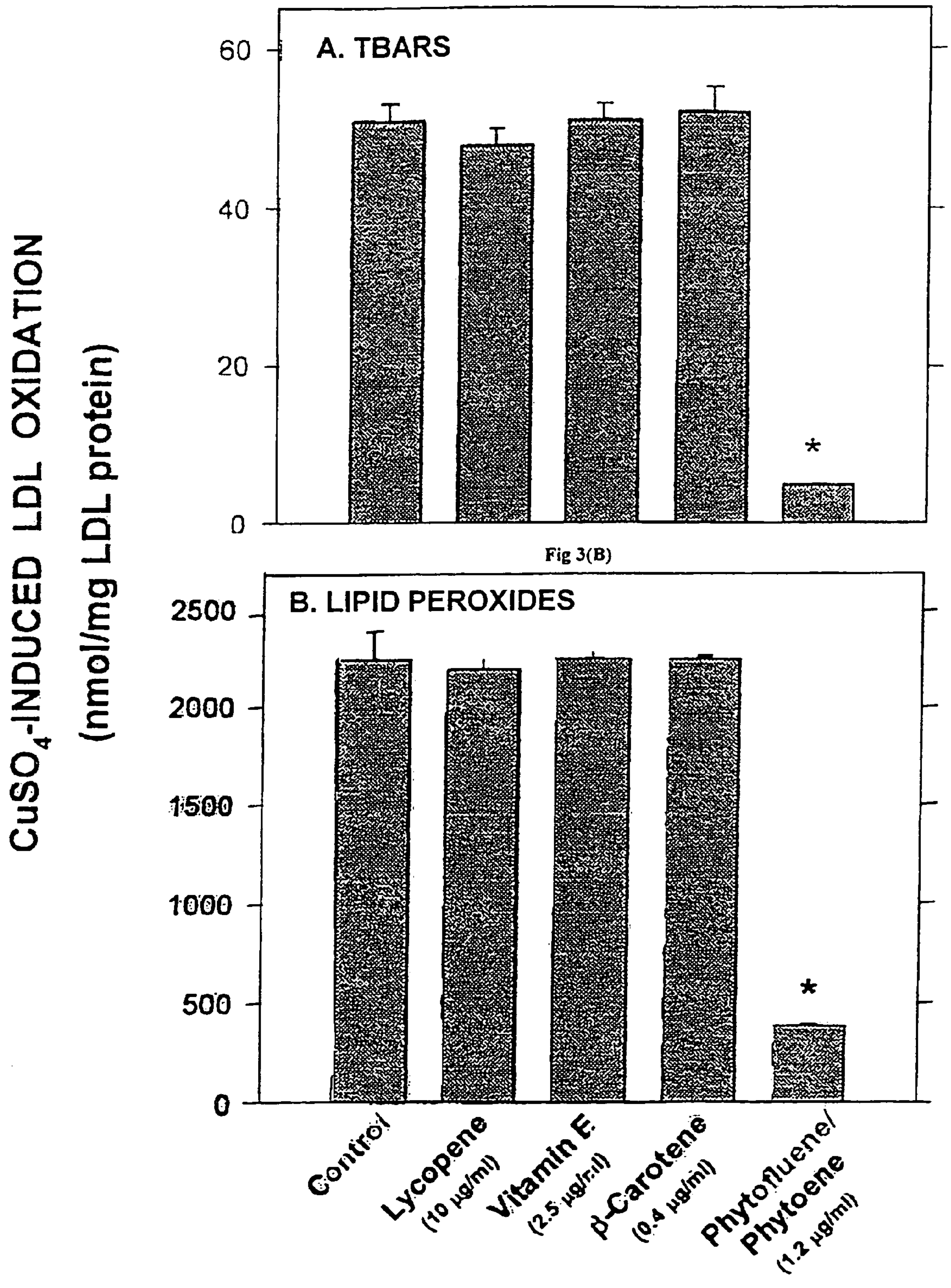
FIG. 3(A), (B)—Effect of lycopene, vitamin E, β-carotene, and phytofluene/phytoene on LDL oxidation.

Effect of Crystalline Natural Lycopene and of Tomato Oleoresin on Copper Ion-Induced LDL Oxidation: Concentration Study LDL (100 μg of protein/mL) was pre-incubated for 30 minutes at 37° C. with increasing concentrations of crystalline pure lycopene, or with tomato oleoresin (at equivalent lycopene concentrations), followed by a further incubation for 2 hours at 37° C. in the presence of 5 μmol/L of $CuSO_4$. LDL oxidation was measured by the TBARS (A) or by the lipid peroxides (B) assays respectively. Results are given as mean±SD (n=3). Addition of increasing concentrations of lycopene inhibited copper ion-induced LDL oxidation moderately, in a dose-dependent manner. A maximal 22% and 27% inhibition in TBARS (FIG. 1A) and in lipid peroxides (FIG. 1B) formation, respectively, was obtained on using 50 μmol/L of lycopene. However, addition of tomato oleoresin to the lipoprotein, inhibited LDL oxidation to a much greater extent (about 90% inhibition), with an $IC_{50}$ (the concentration needed to inhibit LDL oxidation by 50%) of 8.0 μmol/L and 8.4 μmol/L of lycopene equivalents for the inhibition of TBARS (FIG. 1A) and of lipid peroxides (FIG. 1B) formation, respectively.

Example 2

Effect of Phytofluene/Phytoene on Copper Ion-Induced LDL Oxidation: Concentration Study Phytofluene/phytoene dose-dependently inhibited $CuSO_4$-induced LDL oxidation, as measured by the TBARS 2(A) and by the lipid peroxides assays 2(B), respectively. The $IC_{50}$ of Phytofluene/phytoene in the copper ions-induced LDL oxidation is 0.25 μg/ml for inhibition of TBARS formation and 0.35 μg/ml for inhibition of lipid peroxides formation, respectively.

Example 3

Effect of Lycopene, Vitamin E, β-Carotene, and Phytofluene/Phytoene on LDL Oxidation At the low concentration, which mimics the composition of Lyc-O-Mato®, Lycopene (10 μg/ml), vitamin E (2.5 μg/ml) and β-carotene (0.4 μg/ml) did not significantly affect LDL oxidation. In contrast, phytofluene/phytoene (1.2 μg/ml) substantially inhibited LDL oxidation by 85-90% as analyzed by TBARS and lipid peroxides assays.

Example 4

Effect of Lycoepene in Combination with Antioxidants on LDL Oxidation

Figures 4A, 4B:
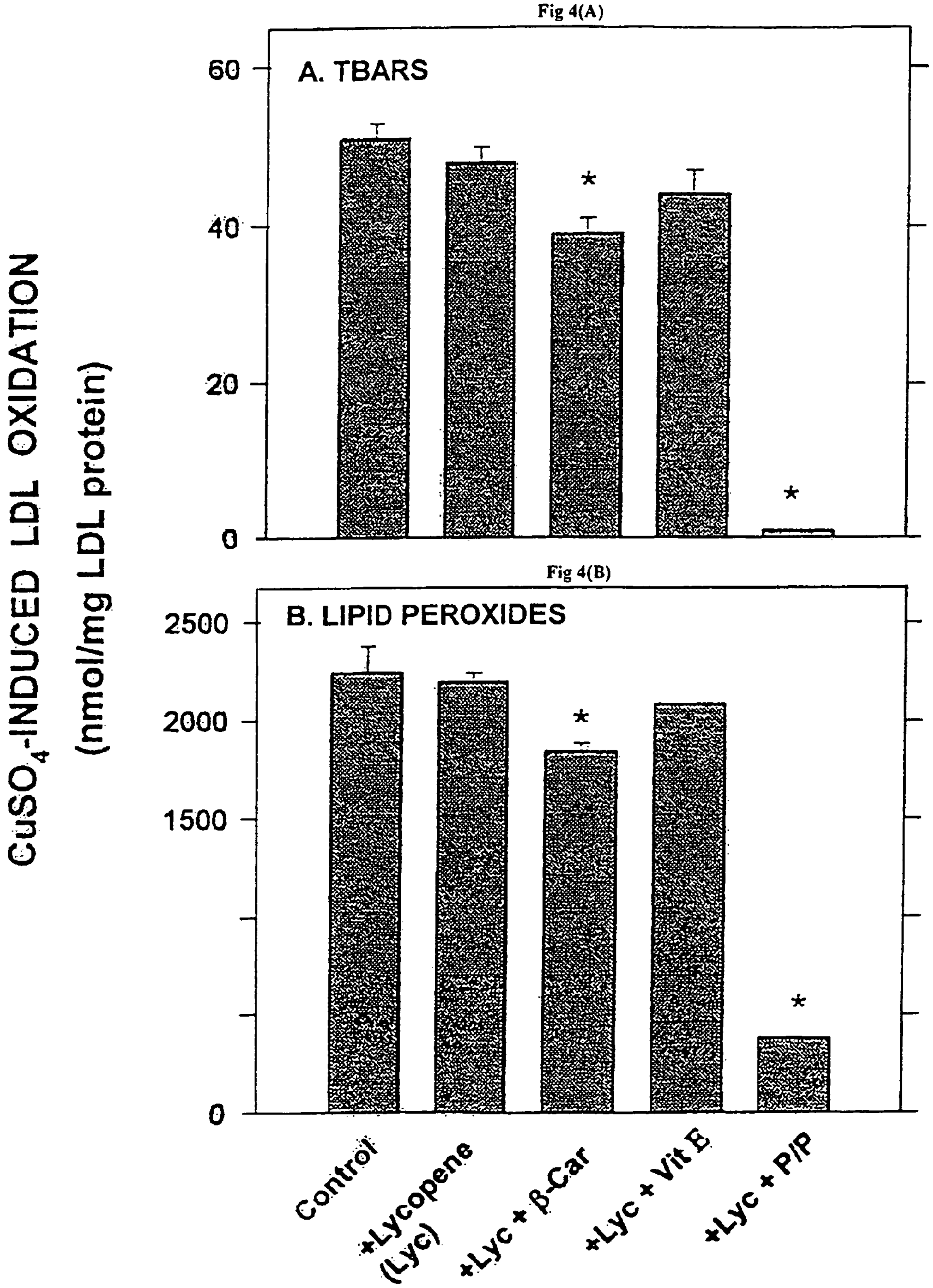
FIG. 4(A), (B)—Effect of lycopene in combination with antioxidants on LDL oxidation.

On using Lycopene (10 μg/ml) in combination with each one of the other antioxidants separately (2 compound in each study), the addition to lycopene to β-carotene (0.4 μg/ml) or vitamin E (2.5 μg/ml) inhibited LDL oxidation (TBARS assay) by 22% and 11% respectively, in comparison to the effect of lycopene alone, whereas the addition of phytofluene/phytoene (1.2 μg/ml) inhibited LDL oxidation by as much as 95%. These results, presented in FIG. 4 show that the addition to lycopene of β-carotene or vitamin E contribute, though minimally, to the inhibition of LDL oxidation, whereas phytofluen/phytoen posses the highest capacity to act as a most potent inhibitor of LDL oxidation (alone, and in combination with lycopene). Similar results were obtained for LDL oxidation analysis by the lipid peroxides assay.

Example 5

Effect of β-Carotene in Combination with Antioxidants on LDL Oxidation

Figures 5A, 5B:
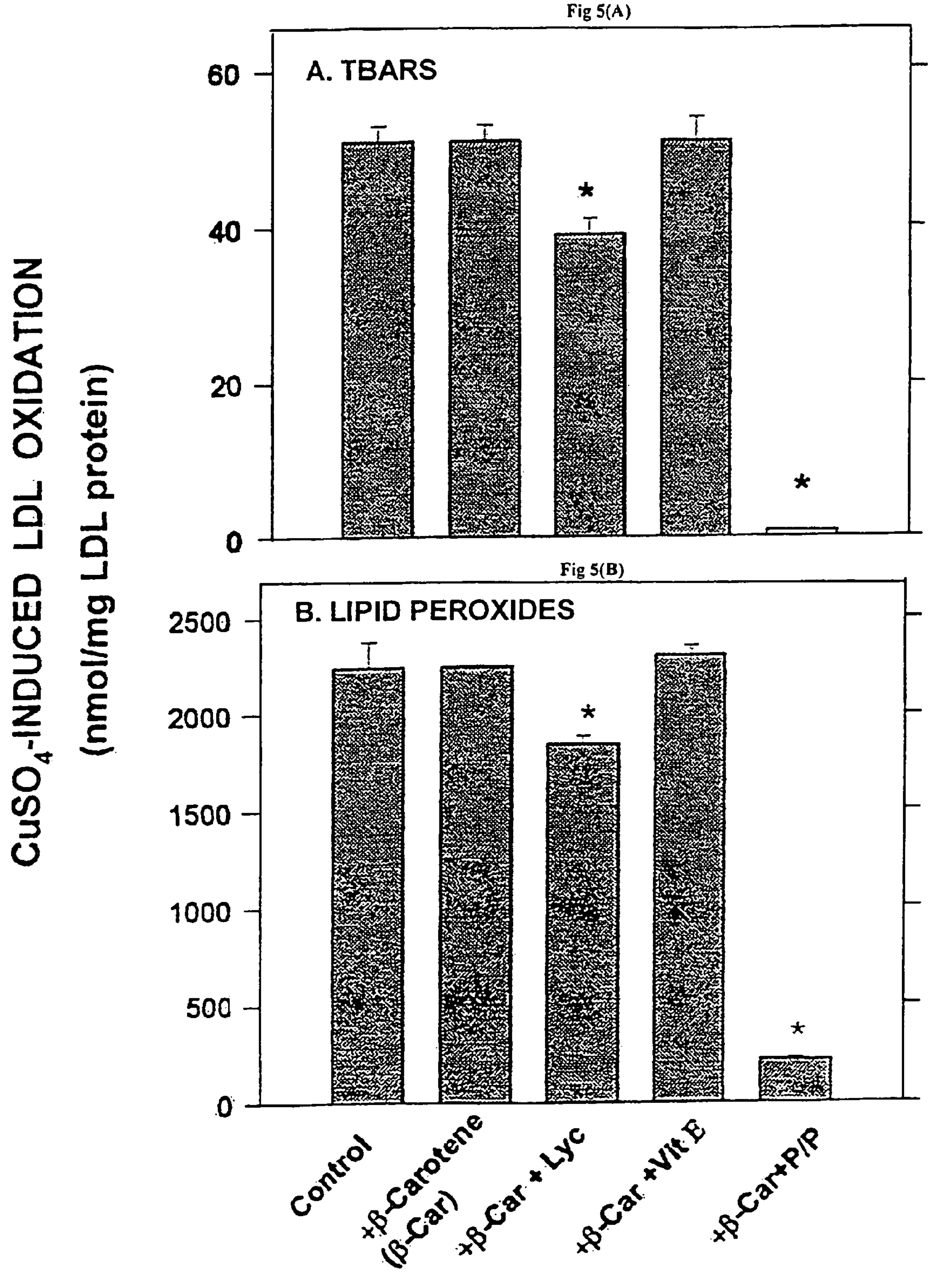
FIG. 5(A), (B)—Effect of β-Carotene in combination with antioxidants on LDL oxidation.

With reference to FIG. 5, on using β-carotene as the major antioxidant alone or in combination with the other antioxidants, unlike lycopene, it did not affect at all LDL oxidation alone or in combination with vitamin E. An inhibitory effect (22%) on LDL oxidation (TBARS) was observed when β-carotene was added in combination with lycopene and a most potent inhibition of LDL oxidation (98% inhibition, in the TBARS assay) was obtained on adding β-carotene together with phytofluene/phytoene. Similar results were obtained for LDL oxidation analyses by the lipid peroxides assay.

Example 6

Effect of Vitamin E in Combination with Antioxidants on LDL Oxidation

Figures 6A, 6B:
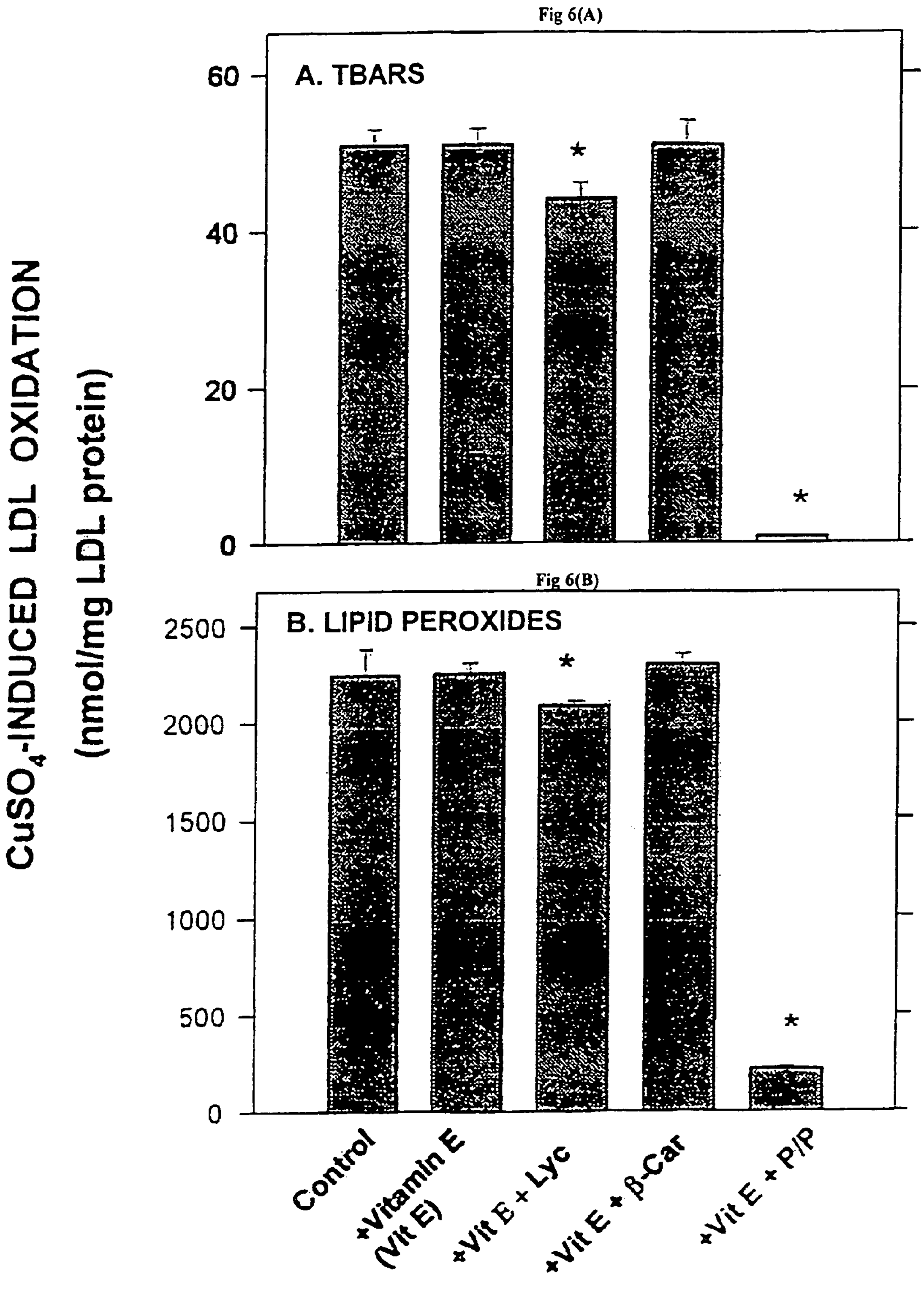
FIG. 6(A), (B)—Effect of vitamin E in combination with antioxidants on LDL oxidation.

On using vitamin E as the major antioxidant alone or in combination with the other antioxidants, the addition of lycopene but not β-carotene, inhibited LDL oxidation by 12% (TBARS assay). The addition of phytofluene/phytoene to vitamin E resulted in a 98% inhibition in LDL oxidation. Similar results were obtained for the lipid peroxides assay as can be seen in FIG. 6.

Example 7

Figure 7A:
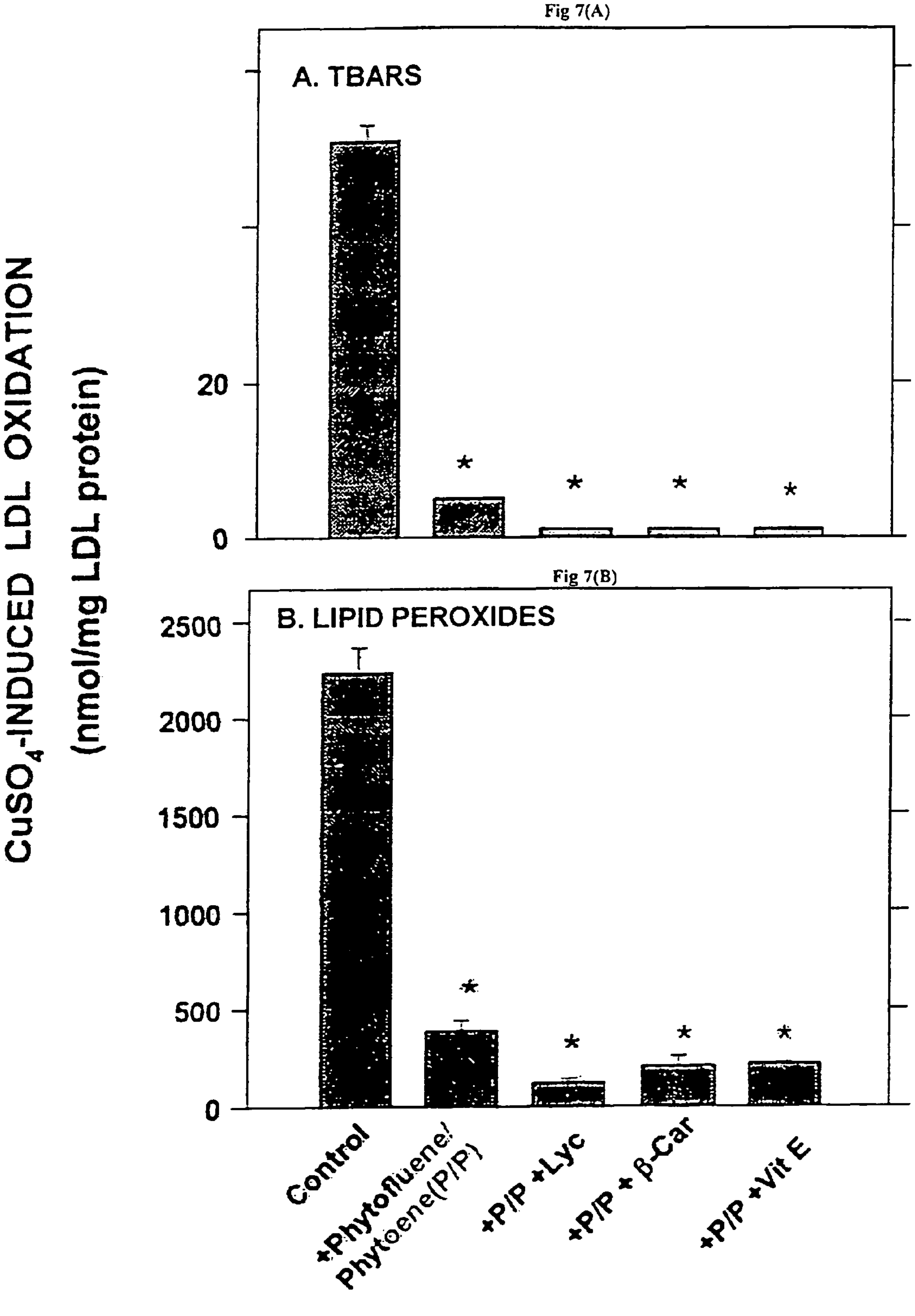
FIG. 7(A), (B)—Effect of phytofluene/phytoene in combination with antioxidants on LDL oxidation.

Effect of Phytofluene/Phytoene in Combination with Antioxidants on LDL Oxidation Referring to FIG. 7, phytofluene/phytoene was found to be the most potent antioxidant among the carotenoids examined, resulting in up to 90% inhibition of LDL oxidation (TBARS assay). The addition of each of the other antioxidant further reduced LDL oxidation with the highest contribution observed for lycopene.

Example 8

Effect of Combination of Antioxidants on LDL Oxidation

Figure 8A:
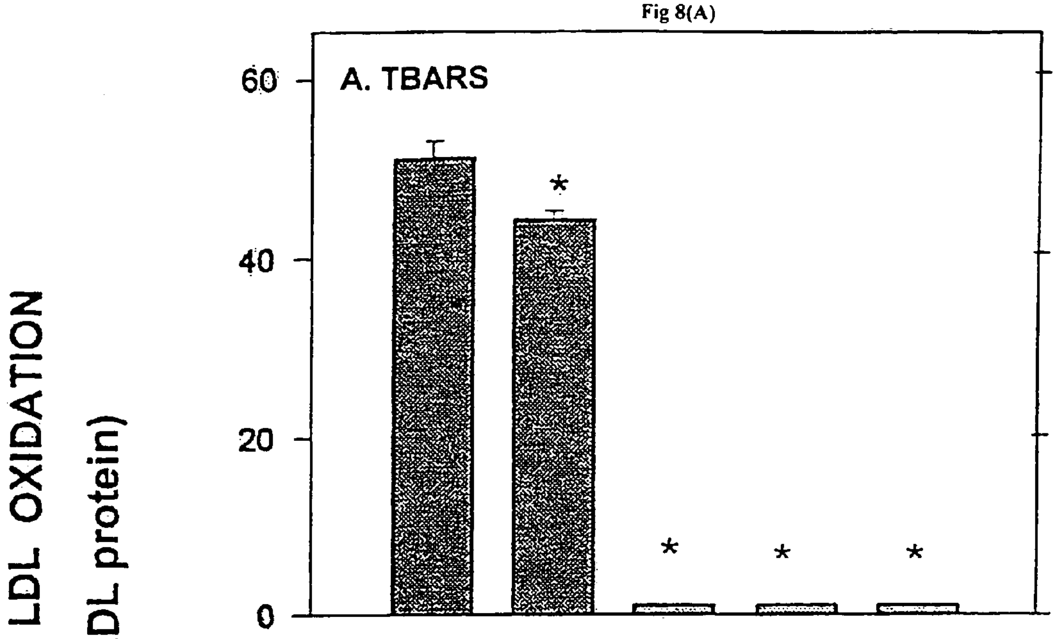
FIG. 8(A), (B)—Effect of combination of antioxidants on LDL oxidation.
Figure 8B:
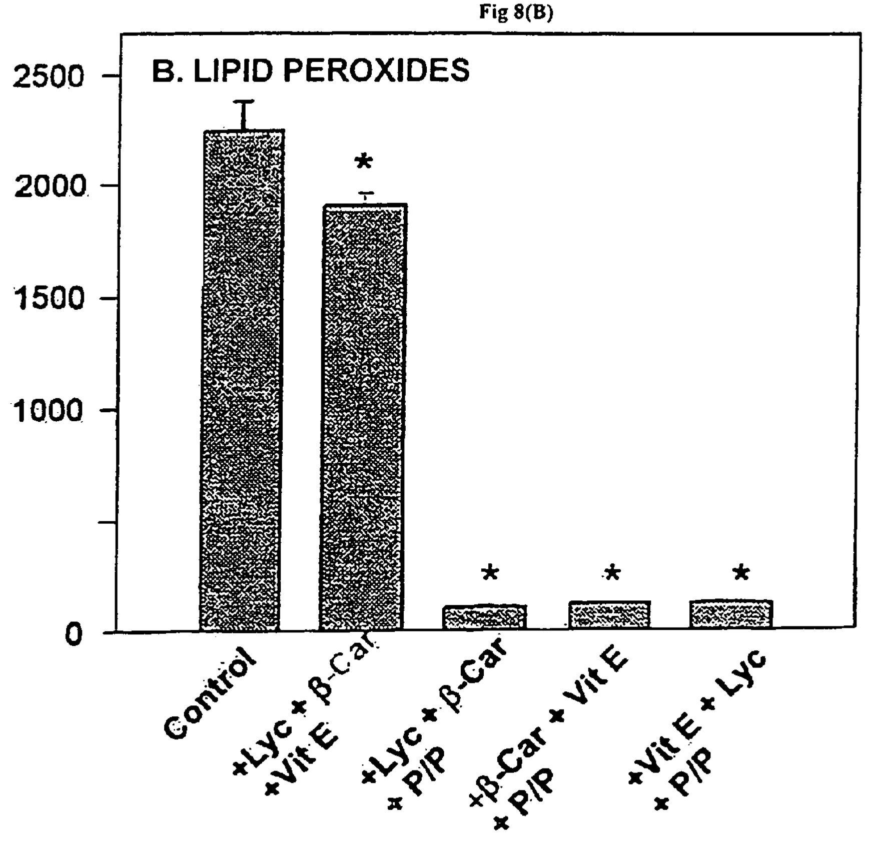

Analysis of the effect of various combinations of 3 antioxidants together were evaluated. Only when the phytofluen/phytoene fraction was present, in any of the 3 studied combinations, a substantial, over 90% inhibition in LDL oxidation was observed. When lycopene, β-carotene and vitamin E were used in combination, in the absence of phylofluene/phytoene, only minimal inhibition of LDL oxidation was obtained as shown for both the TBARS and the lipid peroxide assays in FIG. 8.

Example 9

Effect of a Mixture of Carotenoids on LDL Oxidation

The effect of Lyc-O-Mato® was compared to a mixture of carotenoids prepared from the combination of 5 antioxidant compounds in the following concentrations; lycopene (10 μg/ml), β-carotene (0.4 μg/ml), Vitamin E (2.5 μg/ml) and phytoene/phytofluene (102 μg/ml). Lyc-O-Mato® caused about 70% (TBARS assay) inhibition in LDL oxidation. The carotenoid mixture inhibitory effect on LDL oxidation was 96% (TBARS assay). Similar results were obtained for the lipid peroxides assay.

While embodiments of the invention have been described by way of illustration, it will be apparent that the invention may be carried out with many modifications, variations and adaptations, without departing from its spirit or exceeding the scope of the claims.

The invention claimed is:

1. A method for inhibiting the progression of atherosclerosis, comprising the administration of an effective anti-LDL-oxidation amount of phytoene, phytofluene or mixtures thereof, substantially free of any other active component, to a subject in need thereof.

2. A method according to claim 1 wherein at least 0.2 mg/day thereof are administered to a subject in need thereof.

3. A method according to claim 1 wherein a mixture of phytoene and phytofluene is administered.

4. A method according to claim 3 wherein the ration of phytoene and phytofluene in the mixture is from about 1:20 to about 20:1.

5. A method according to claim 1 wherein administration is in a daily dose.

6. A method according to claim 1 wherein administration is adapted to achieve an anti-LDL-oxidation effective concentration of phytoene, phytofluene or mixtures thereof, in the blood, said concentration being at least 0.01 μM.

* * * * *